United States Patent [19]

Yamada et al.

[11] Patent Number: 4,705,784
[45] Date of Patent: Nov. 10, 1987

[54] CEPHEM COMPOUNDS

[75] Inventors: Hirotada Yamada, Nishinomiya, Japan; Naruhito Masai, Gainesville, Fla.; Sinji Ueda, Nishinomiya, Japan; Takao Okuda, Toyonaka, Japan; Masatomo Fukasawa, Nishinomiya, Japan; Masuhiro Kato, Toyonaka, Japan; Masataka Fukumura, Takarazuka, Japan

[73] Assignee: Sumitomo Pharmaceuticals Company, Limited, Osaka, Japan

[21] Appl. No.: 682,283

[22] Filed: Dec. 17, 1984

[30] Foreign Application Priority Data

Dec. 21, 1983 [JP] Japan ................... 58-242904

[51] Int. Cl.⁴ .................. C07D 501/34; A61K 31/545
[52] U.S. Cl. ..................................... 514/202; 540/222; 540/223
[58] Field of Search ............. 544/22, 16; 514/202; 540/222, 223

[56] References Cited

U.S. PATENT DOCUMENTS

| | | | |
|---|---|---|---|
| 4,024,133 | 5/1977 | Cook et al. | 260/243 C |
| 4,138,555 | 2/1979 | Cook et al. | 544/22 |
| 4,267,320 | 5/1981 | Gregson et al. | 544/22 |
| 4,282,220 | 8/1981 | Bormann et al. | 424/246 |
| 4,411,897 | 10/1983 | Scartazzini | 424/246 |

FOREIGN PATENT DOCUMENTS 1151151 8/1983 Canada.
2089339 6/1982 United Kingdom.

OTHER PUBLICATIONS

The Journal of Antibiotics, 34, 171-185 (1981).

Primary Examiner—Nicholas S. Rizzo
Attorney, Agent, or Firm—Stevens, Davis, Miller & Mosher

[57] ABSTRACT

A cephem compound represent by the general formula

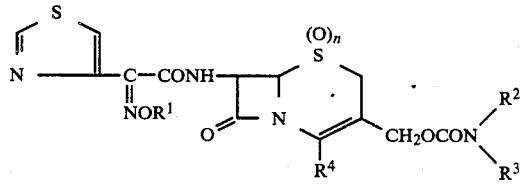

wherein, $R^1$ represents hydrogen or lower alkyl, $R^2$ and $R^3$ are the same or different and each represents hydrogen or lower alkyl, $R^4$ represents carboxyl or esterified carboxyl, and n represents 0 or 1, a salt of the cephem compound, and a process for producing the cephem compound or a salt thereof. Compounds of the above formula and salts thereof are valuable as antibacterial agents and are especially useful as oral drugs in the prevention or treatment of bacterial infectious diseases.

20 Claims, No Drawings

CEPHEM COMPOUNDS

The present invention relates to novel cephem compounds, and more particularly to cephem compounds represented by the general formula

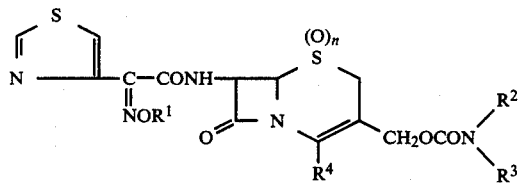

(wherein $R^1$ represents hydrogen or lower alkyl, $R^2$ and $R^3$ are the same or different and each represents hydrogen or lower alkyl, $R^4$ represents carboxyl or esterified carboxyl, and n represents 0 or 1) and to salts thereof.

The lower alkyl group represented by $R^1$ in formula (I) above includes $C_1$-$C_4$ alkyls, e.g. methyl, ethyl, n-propyl, isopropyl, n-butyl, and tert-butyl. The lower alkyl group represented by $R^2$ or $R^3$ includes also $C_1$-$C_4$ alkyls, e.g. methyl, ethyl, n-propyl, isopropyl, and n-butyl.

The esterified carboxyl groups represented by $R^4$ is a group which can give a free carboxyl group by hydrolysis after absorption of the corresponding cephem compound in the living body, and includes, e.g. lower alkoxycarboxyl, substituted lower alkoxycarbonyl, lower alkenyloxycarbonyl, lower alkynyloxycarbonyl, aryloxycarbonyl, substitued aryloxycarbonyl, and phthalidyloxycarbonyl. The substituent of the substituted lower alkoxycarbonyl group mentioned above includes, e.g. lower alkanoyloxy, lower alkoxycarbonyloxy, lower alkoxy, lower alkylthio, lower alkanesulfonyl, aryl, substituted or unsubstituted benzoyl, 5-lower alkyl-2-oxo-1,3-dioxolen-4-yl, and 5-aryl-2-oxo-1,3-dixolen-4-yl. The alkyl part of the substituted lower alkyl group mentioned above includes $C_1$-$C_4$ alkyls, e.g. methy, ethyl, n-propyl, isopropyl, and n-butyl.

Such esterified carboxyl groups may be represented by the general formula —COOR. Examples of the R group are as follows: lower alkanoyloxyalkyls, e.g. acetoxymethyl, propionyloxymethyl, butyryloxymethyl, isobutyryloxymethyl, valeryloxymethyl, pivaloyloxymethyl, hexanoyloxymethyl, 1-acetoxyethyl, 1-propionyloxyethyl, and 1-acetoxypropyl; lower alkoxycarbonyloxyalkyls, e.g. methoxycarbonyloxymethyl, 1-methoxycarbonyloxyethyl, 1-methoxycarbonyloxypropyl, ethoxycarbonyloxymethyl, propyloxycarbonyloxymethyl, 1-ethoxycarbonyloxyethyl, and 1-propyloxycarbonyloxyethyl; lower alkyls, e.g. methyl, ethyl, propyl, isopropyl, butyl, isobutyl, tert-butyl, pentyl, and hexyl; lower alkenyls, e.g. vinyl and allyl; lower alkynyls, e.g. ethynyl and propynyl; lower alkoxyalkyls, e.g. methoxymethyl, ethoxymethyl, isopropoxymethyl, 1-methoxyethyl, and 1-ethoxyethyl; lower alkylthioalkyls, e.g. methylthiomethyl, ethylthiomethyl, isopropylthiomethyl, and ethylthioethyl; lower alkanesulfonylalkyls, e.g. mesylmethyl and 2-mesylethyl; ring-substituted or unsubstituted phenylalkyls, e.g. benzyl, 4-methoxybenzyl, phenethyl, 3-chlorobenzyl, 3-fluorobenzyl, 3-methylbenzyl, 3-methoxybenzyl, 4-methoxybenzyl, and 3,4-dimethoxybenzyl; arylmethyls, e.g. 2-furylmethyl and 2-thienylmethyl; substituted or unsubstituted aryls, e.g. phenyl, tolyl, xylyl, and indanyl; substituted or unsubstituted phenacyls, e.g. phenacyl and p-chlorophenacyl; 5-lower alkyl substituted (or 5-aryl substituted)-2-oxo-1,3-dioxolen-4-ylmethyls, e.g. 5-methyl-2-oxo-1,3-dioxolen-4-ylmethyl; and phthalidyl.

Preferred examples of the R group are lower alkanoyloxyalkyls and lower alkoxycarbonyloxyalkyls. More preferred examples of the R group are pivaloyloxymethyl, 1-ethoxycarbonyloxyethyl and 1-acetoxyethyl.

Compounds of the formula (I) wherein $R^4$ is carboxyl are capable for forming salts. Such salts include; alkali metal salts, e.g. sodium salts and potassium salts; alkaline earth salts, e.g. calcium salts and magnesium salts; organic amine salts, e.g. triethylamine salts, diethanolamine salts, pyridine salts, picoline salts, N,N'-dibenzylethylenediamine salt, morpholine salts, and procaine salts; and amino acid salts, e.g. L-arginine salts and L-lysine salts.

The 7-positional residue

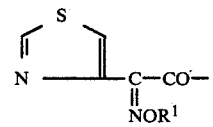

in formula (I) involves geometric isomers of syn form and anti form. The syn form is preferred in the invention.

The compound of the present invention is useful as antibiotics for prevention or treatment of infectious diseases of poultry or mammals including human beings or as a intermediate for production of such antibiotics.

In recent years antibiotics of a cephem group are under remarkble development as therapeutic agents for the treatment of infectious diseases. Compounds of this group are now commercially available which have high antimicrobial activity and wide antimicrobial spectra. However, these compounds are scarcely absorbed when orally administered, so that therapeutic effect thereof is achievable only through injection.

Compounds such as cephalexin, cefatrizine, cefaclor, although in use as cephem antibiotics for oral administration, are slightly inferior in antimicrobial activity and width of a antimicrobial spectrum and ineffective on β-lactamase producing resistant bacteria. It is therefore desired to develop a compound improved in the above noted properties.

On the other hand, there are in clinical use certain penicillin compounds which, so-called prodrugs, have been improved in oral absorbability by esterification of the carboxyl group of penicillin. It is considered that the esterified compound, absorbed in the living body, is hydrolyzed into the original free acid by enzymes present, for example, in the serum or tissues of the body, thus exhibiting the effect. Similar modifications of cephalosporin compounds have been attempted, but no compound having an oral dosage absorbability sufficient for clinical use has been found until now. That is, some ester groups effective in penicillin compounds for enhancing the oral dosage absorbability is not always so effective in cephalosporin compounds.

The present inventors made extensive studies of cephalosporin compounds for the improvement in oral dosage absorbability by the prodrug method. It has proved therefrom that the absorbability after oral administration is unpredictable at all and depends upon the structure and properties of the parent compound.

Based on such knowledge, this invention has been accomplished. Compounds represented by formula (I) are superior antibiotics having high oral dosage absorbability unexpectable from known compounds of analogous structure.

Among the compounds represented by formula (I), those of the formula wherein n is 0 and $R^4$ is carboxyl have high antimicrobial activity against gram-positive bacteria and gram-negative bacteria and additionally against β-lactamase-producing resistant bacteria. These compounds are hence useful as such and also as intermediates for compounds having esterified carboxyl as $R^4$. Compounds of the formula (I) wherein n is 0 and $R^4$ is esterified carboxyl are excellent because of their good absorbability when administered orally. After absorption, the compounds are converted into parent compounds that have free carboxyl as $R^4$ and thus exhibit the effect. Hence these ester compounds are very valuable as oral drugs in the prevention or treatment of bacterial infectious diseases.

Among the compounds of the invention, sulfoxide compounds, i.e. the compounds of the formula (I) wherein n is 1, are useful as intermediates for producing ester compounds of the formula (I) wherein $R^4$ is esterified carboxyl. Further details of these intermediates will be described later.

The compounds of the invention can be produced by processes which themselves are known, for example as follows:

PROCESS (a)

A derivative of 7-amino-3-carbamoyloxymethyl-3-cephem-4-carboxylic acid represented in the general formula

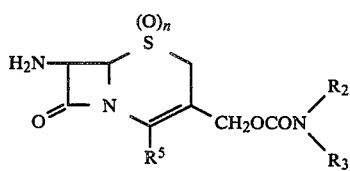

(n, $R^2$, and $R^3$ are as defined above and $R^5$ has the same meaning as does the above $R^4$ or represents protected carboxyl) is acylated with a compound represented by the general formula

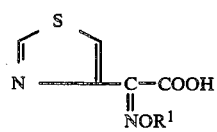

($R^1$ is as defined above), and if necessary, the protecting group is eliminated or the carboxyl group is esterified.

PROCESS (b)

A compound represented by the general formula

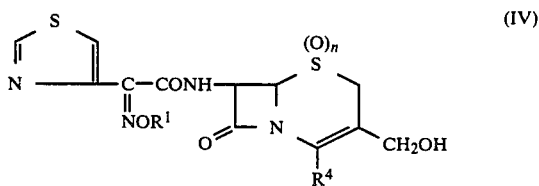

($R^1$, $R^4$, and n are as defined above) is treated to replace the hydrogen atom of the 3-positional hydroxymethyl group by an N,N-substituted or unsubstituted carbamoyl group.

PROCESS (c)

The acyl group attached to the 7-positional nitrogen atom of the compound of formula (I) is derived from another acyl group which is first attached to said nitrogen atom.

Processes (a), (b), and (c) are described below in more detail.

PROCESS (a)

The compound represented by the general formula

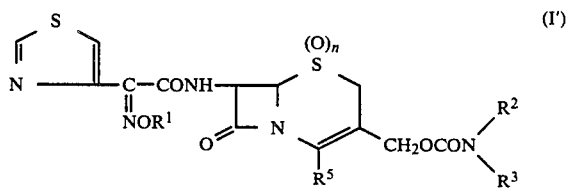

(n, $R^1$, $R^2$, $R^3$, and $R^5$ are as defined above) or a salt thereof can be obtained by reacting a carboxylic acid represented by formula (II) above or a reactive derivative thereof with a compound represented by formula (III) above or a salt thereof. When the residue represented by $R^5$ is carboxyl or a salt thereof, a compound of the invention represented by formula (I) above can be obtained by esterifying further said obtained compound if necessary. When the residue represented by $R^5$ is a protected carboxyl group, the protecting group is removed from said obtained compound, and if necessary, is esterified.

The above reactive derivative of a compound represented by formula (II) above means a reactive derivative of carboxyl group which can react with a compound represented by formula (III) above to form an amido linkage. Such reactive derivatives include, for example, acid halides, acid anhydrides, acid azolides, active esters, and acid azides of carboxylic acids (formula (II)). More particularly, examples thereof are; acid halides, e.g. acid chloride and acid bromide; mixed acid anhydrides with e.g. dialkyl phosphate, phenylphosphoric acid, diphenyl phosphate, dibenzyl phosphate, dialkyl phosphorous acid, methanesulfonic acid, toluenesulfonic acid, naphthalenesulfonic acid, alkyl hydrogencarbonates, aliphatic carboxylic acids (e.g. pivalic acid, pentanoic acid, isopentanoic acid, and 2-ethylbutanoic acid), and aromatic carboxylic acids; symmetric acid anhydrides; acid azolides with, e.g. imidazole, substituted imidazole, dimethylpyrazole, triazole, and tetrazole; active esters, e.g. cyanomethyl ester, methoxymethyl ester, p-nitrophenyl ester, 2,4-dinitrophenyl ester, trichlorophenyl ester, pentachlorophenyl ester, methanesulfonylphenyl ester, phenylthiohexyl ester, p-nitrophenylthio ester, p-cresylthio ester, carboxymethylthio ester, pyranyl ester, pyridyl ester, piperidyl ester, and 8-quinolyl-thio ester, and esters with, e.g. N,N-dimethylhydroxylamine, 1-hydroxy-2(1H)-pyridone, N-hydroxysuccinimide, N-hydroxyphthalimide, and hydroxybenzotriazole.

When the compound represented by formula (II) above is used in the form of free acid or salt thereof, this amidation can be carried out in the presence of a condensing agent. For the condensing agent, there may be used, for example, N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, N,N'-carbonylbis(2-methylimidazole), pentamethyleneketene-N-cyclohexylimine, diphenylketene-N-cylohexylimine, alkoxyacetylenes, 1-alkoxy-1-chloroethylenes, trialkyl phosphites, ethyl polyphosphate, isopropyl polyphosphate, phosphorus oxychloride, phosphorus trichloride, thionyl chloride, oxalyl chloride, triphenylphosphine, 2-ethyl-7-hydroxylbenzisoxazolium salt, 2-ethyl-5-(m-sulfonyl)isoxazolium hydroxide inner salt, (chloromethylene)dimethylammonium chloride, and Vilsmeier's reagent prepared, e.g. from phosphorus oxychloride and dimethylformamide.

As stated above, amidation techniques generally used in the field of peptide chemistry, penicillin and cephalosporin chemistry, or some other fields can be applied in the invention.

Suitable salts of the compound of formula (III) above include, for example; salts of the compound with alkali or alkaline earth metals such as sodium, potassium, and calcium; salts thereof with organic bases such as trimethylamine, triethylamine, quinoline, and collidine; salts thereof with organic sulfonic acids such as toluenesulfonic acid, naphthalenesulfonic acid, and tetralinsulfonic acid; and salts thereof with inorganic acids such as hydrochloric acid, sulfuric acid, and nitric acids.

Examples of $R^5$ in formula (III) above are carboxyl groups protected by esterification or amidation in addition to the esterified carboxyl groups cited above as examples of $R^4$. Preferred protected carboxyl groups are those which, after acylation, are readily decomposed into free carboxylic acid residues, for example, by hydrolysis or alcoholysis in acidic or weak alkaline media, hydrogenolysis, reduction, oxidation, nucleophilic substitution, photochemical reaction, or enzymatic reaction. Such protected carboxylic derivatives include known protected carboxylic esters, e.g. silyl ester, organic tin ester, toluenesulfonylethyl ester, p-nitrobenzyl ester, diphenylmethyl ester, trityl ester, trichloroethyl ester, phthalimidomethyl ester, 2-nitrobenzyl ester, and 2,2'-dinitrobenzyl ester. In the case of silyl ester, the other site that can be silylated, i.e. the amino group, may be silylated as well.

The reaction of the compound represented by formula (II) with the compound represented by formula (III) is usually carried out in an inert solvent consisting of a polar solvent, a nonpolar solvent and/or a mixture of them; a polar solvent such as dichloromethane, chloroform, acetone, tetrahydrofuran, dioxane, acetonitrile, methyl isobutyl ketone, dimethylformamide, dimethylacetamide, dimethylsulfoxide, hexamethylphosphoric triamide, or sulfolane; a nonpolar solvent, such as benzene, toluene, petroleum ether, or n-hexane. In certain cases, mixtues of water and these solvents can be used.

The above reaction can be effected at any possible temperature, usually up to 50° C.

Thus the compound represented by formula (I') above can be produced. When the residue represented herein by $R^5$ is carboxyl or a salt thereof, the compound of the formula (I) wherein $R^4$ is an esterified carboxyl group can be produced by the reaction of an esterifying agent on the carboxyl or the salt thereof.

The esterification can be accomplished by methods which themselves are known. For instance, a compound of the formula (I') wherein $R^5$ is an alkali metal salt of carboxyl group can be esterified by reacting in an inert solvent with a halide (preferably bromide, iodide, or chloride) of the alcohol residue of the intended ester. The method of esterification in the presence of a crown ether or a phase transfer catalyst, the method itself being already known, can be applied to this reaction. The esterification is favorably accomplished in the presence of an organic base such as triethylamine or in the presence of an inorganic base such as sodium carbonate or potassium carbonate.

When an alcohol is used as esterifying agent, the reaction is carried out desirably in the presence of a condensing agent. Such a condensing agent includes; carbodiimide compounds, e.g. N,N'-dicyclohexylcarbodiimide, N,N'-diethylcarbodiimide, and N-cyclohexyl-N'-(4-diethylaminocyclohexyl)carbodiimide; sulfonic acid esters of N-hydroxybenzotriazole derivatives, e.g. 1-(4-chlorobenzenesulfonyloxy)-6-chloro-1H-benzotriazole; benzenesulfonic acid chloride; and so-called Vilsmeier's reagent, which is prepared by reacting dimethylformamide with a halogen compound such as thionyl chloride or phosphorus oxychloride.

The reaction temperature is not particularly limited, but it is usually up to 50° C. Inert solvents suitable for the amidation which is described above can also be used in this esterification.

The product of the esterification, when a sulfide of the formula (I) wherein n is 0 is used as a starting material, may contain 2-cephem isomer thereof as an impurity. The 2-cephem isomer can be removed by subjecting the reaction product to recrystallization, reprecipitation, column chromatography, etc. Alternatively, the 2-cephem-containing product is converted into 3-cephem-1-oxide form by oxidation with m-chloroperbenzoic acid, peracetic acid, periodic acid, or the like, and then the oxide is reduced, for example, by phosphorus trichloride or by a combination of acetyl chloride with stannous chloride, whereby the intended 3-cephem ester product can be obtained in substantially pure form. The sulfur atom in the cephem ring can be oxidized according to the usual method. This reaction may yield (S)- and (R)-oxides depending upon the oxidant used. Both the oxides are included in the scope of this invention. The oxidation and reduction of the sulfur atom in the cephem ring are described, for example, in "Cephalosporins and Pencillins Chemistry and Biology" edited by E. Flynn (Academic Press, 1972), Chapter 4, p. 135.

The starting compound represented by formula (II) is prepared, for example, according to a process described in Japanese Patent Application Laid-Open No. 154,785/79 or 133,385/80.

The starting compound represented by formula (III) can be prepared according to conventional processes, for example, techniques described in U.S. Pat. No. 3,905,963 and U.K Pat. Nos. 1041,985 and 1,350,772.

PROCESS (B)

The compound represented by formula (I) above can be produced from the compound of the general formula (IV):

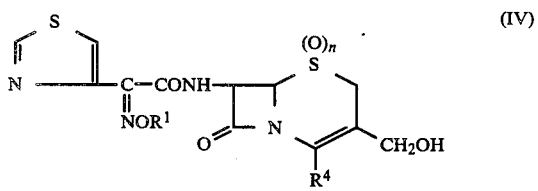

($R^1$, $R^4$, and n are as defined above) by converting the 3-positional hydroxymethyl group into a N,N-substituted or unsubstituted carbamoyloxymethyl group. Methods themselves known are applicable to the carbamoyl forming reaction (see, e.g. "Recent Advances in the Chemistry of β-Lactam Antibiotics, Second International Symposium 1980" edited by G. I. Gregory, Chapter 3, p. 38, The Royal Soceity of Chemistry, Burlington House, London, Wlv OBN).

The starting compound of formula (IV) can be prepared from the carboxylic acid of formula (II) and a derivative of 7-amino-3-7-amino-3-hydroxymethyl-cephalosporin in the same manner as described for the preparation of the compound of formula (I') by reacting the compound of formula (II) with the compound of formula (III).

PROCESS (C)

The 7-positional acyl group of the compound represented by formula (I) can be derived chemically from another acyl group, for example, by the following processes:

A process comprising reacting a carboxylic acid represented by the formula

or a reactive derivative thereof with the compound of formula (III) or a salt or derivative thereof, and reacting the resulting compound represented by the general formula

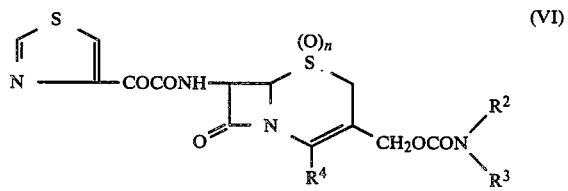

(n, $R^2$, $R^3$, and $R^4$ are as defined above) with an amine represented by the general formula $R^1ONH_2$ ($R^1$ is as defined above) to give the compound of the invention represented by formula (I).

A process comprising converting the 3-positional hydroxymethyl group of a compound represented by the formula (VII),

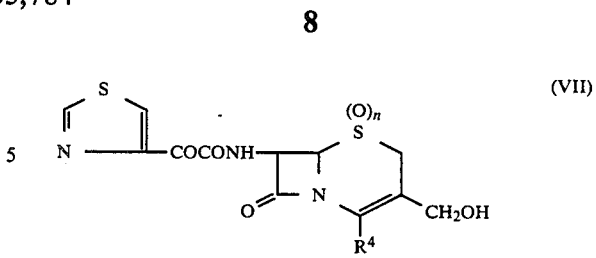

($R^4$ and n are as defined above) into a N,N-substituted or unsubstituted carbamoyloxymethyl group to obtain a compound represented by the formula (VIII),

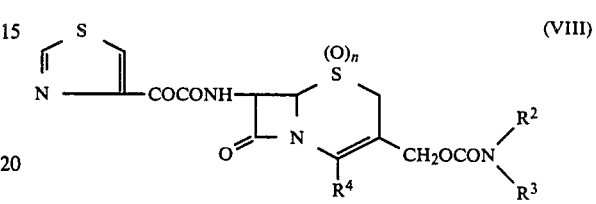

($R^2$, $R^3$, $R^4$ and n are as defined above) and reacting this compound with an amine of the general formula $R^1ONH_2$ ($R^1$ is as defined above) to give the compound of the invention represented by formula (I).

A process comprising reacting thioformamide with a compound represented by the general formula (IX),

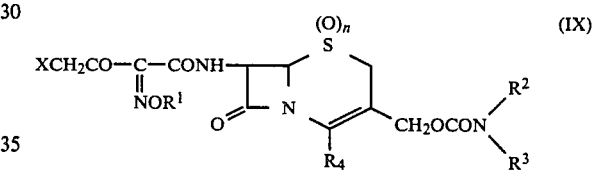

($R^1$, $R^2$, $R^3$, $R^4$, and n are as defined above; X represents chlorine or bromine) to give the compound of the invention represented by formula (I).

A carboxylic acid represented by formula (V) is a known compound described, for example, in Japanese Patent Application Laid-Open No. 154,785/79.

The process for producing the compound of formula (VI) by reacting the compound of formula (V) with the compound of formula (III) can be operated in the same manner as the above described process for producing the compound of formula (I) by reacting the compound of formula (II) with the compound of formula (III).

The reaction of the compound represented by formula (VI) with the amine of the general formula $R^1ONH_2$ ($R^1$ is as defined above) can be carried out according to known methods (e.g. Japanese Patent Application Laid-Open No. 53,096/79).

The reaction of the compound represented by formula (VII) to convert the 3-positional hydroxymethyl group into a carbamoyloxymethyl group can be carried out as described in Process (b) above.

The compound represented by formula (IX) also can be prepared according to known methods (e.g. Japanese Patent Application Laid-Open No. 135,996/78).

The reaction of thioformamide with the compound represented by formula (IX) to produce the compound of formula (I) can also be carried out under known conditions.

As stated before, the compound of the invention having an esterified carboxyl group as $R^4$ is useful as an antibiotic drug suitable for oral administration because of its excellent oral dosage absorbability. For oral administration, the compound of the invention can be made up into capsules, powders, granules, tablets, and the like according to conventional formulations for oral dosage. These pharmaceutical compositions may contain excipients, binders, lubricants, disintegrating agents, etc. The compound of formula (I) can be made up also into rectal dosage form (e.g. suppository or retention clyster) or injectable form.

Suitable doses of the compound, though dependent upon the age, weight, and conditions of patients, are generally 0.05 to 2 g per day for an adult. Such a quantity of the compound may be administered in signal or divided doses.

To manifest excellent properties of compounds of the invention, results of tests thereof for oral dosage absorbability and for antimicrobial activity are shown below.

Results of oral dosage absorbability tests

| Test compd. (Example No.) | Urinary excretion rate after oral administration (dose: 50 mg/kg) | |
|---|---|---|
| | Mouse | Rat |
| 5 | 64% | 30% |

Results of antimicrobial activity tests

| Test compd. (Example No.) | MIC ($\mu$g/ml) | | | | |
|---|---|---|---|---|---|
| | Staphylococcus epidermidis | Escherichia coli | Proteus mirabilis | Serratia marcescens | Enterobacter aerogenes |
| 1 | 1.56 | 0.05 | ≦0.013 | 1.56 | 0.39 |
| 10 | 3.13 | 0.20 | 0.05 | 3.13 | 0.78 |
| 16 | 1.56 | 0.39 | 0.78 | 3.13 | 1.56 |

The present invention is illustrated in more detail by the following examples; however the invention is not limited by these examples.

EXAMPLE 1

7-[(Z)-2-Methoxyimino-2-(thiazol-4-yl)acetamido]-3-carbamoyloxymethyl-3-cephem-4-carboxylic acid To an ice-cooled solution of dimethylformamide (0.402 g) in tetrahydrofuran (10 ml) was added phosphorus oxychloride (0.843 g) and the mixture was stirred at the same temperature for 30 min. To the reaction mixture (Z)-2-methoxyimino-2-(thiazol-4-yl)acetic acid (0.93 g) was added and stirred for 30 min in an ice-cooled bath.

On the other hand, 7-amino-3-carbamoyloxymethyl-3-cephem-4-carboxylic acid (1.365 g) was suspended in a mixture of water (10 ml) and tetrahydrofuran (15 ml). While cooling with ice, triethylamine (1.01 g) was added to form a solution. To this ice-cooled solution was added dropwise the above active solution of (Z)-2-methoxyimino-2-(thiazol-4-yl)acetic acid over one hour. During the time triethylamine (total 0.78 g) was added in parts at suitable times to keep the reaction mixture at pH 6–7. After completion of the dropping, the mixture was stirred for 45 min under cooling with ice. Then the temperature was raised gradually to 15° C. After the mixture was stirred for 20 minutes at that temperature, the tetrahydrofuran was evaporated under reduced pressure. Then the aqueous layer was adjusted to pH 2–3 with 2N-HCl. The precipitates were filtered, washed with water, and dried in vacuo over phosphorus pentoxide to give the title compound (0.90 g). Further, ethyl acetate (20 ml) was added to the filtrate and the mixture was shaken. The insoluble matter formed on the interface between the aqueous layer and the ethyl acetate layer was filtered, and dried in vacuo over phosphorus pentoxide to give the title compound (0.61 g).

$^1$H-NMR (DMSO-d$_6$) $\delta$ value: 3.48, 3.59 (ABq, 2H, J=18 Hz), 3.92 (s, 3H), 4.67, 4.90 (ABq, 2H, J=13 Hz), 5.17 (d, 1H, J=5 Hz), 5.86 (dd, 1H, J=8, 5 Hz), 6.59 (broad s, 2H), 7.93 (d, 1H, J=2 Hz), 9.14 (d, 1H, J=2 Hz), 9.66 (d, 1H, J=8 Hz).

Example 2

7-[(Z)-2-Methoxyimino-2-(thiazole-4-yl)acetamido]-3-carbamoyloxymethyl-3-cephem-4-carboxylic acid (a) (Z)-2-Methoxyimino-2-(thiazol-4-yl)acetic acid (18.6 g) was dissolved in dimethylformamide (100 ml). To the solution were added a solution of 1-hydroxybenzotriazole (13.5 g) in dimethylformamide (100 ml) and then dicyclohexylcarbodiimide (22.7 g). The mixture was stirred at 30° C. for 2 hours. The formed urea compound was removed by filtration. The filtrate was added dropwise to cold water (1250 ml). The mixture was stirred for one hour under cooling with ice. The formed precipitate was filtered, washed with water, and dried under reduced pressure to give an active ester compound (29.3 g).

IR (nujol): 1820, 1725 cm$^{-1}$ $^1$H-NMR(DMSO-d$_6$) $\delta$ value: 4.00 (s, 3H), 7.6–8.4 (m, 4H), 8.38 (d, 1H, J=2 Hz), 9.17 (d, 1H, J=2 Hz).

(b) 7-Amino-3-carbamoyloxymethyl-3-cephem-4-carboxylic acid (5.46 1 g) was suspended in a solution of triethylamine (6.06 g) in diamethylformamide (60 ml). The active ester (6.28 g) from (a) above was added to the suspension. After stirring for 3 hours, the reaction mixture was poured into ether (600 ml) to give oily matter, which was separated. Then water (80 ml) was added to the oily matter. Therefrom was removed insoluble matter by filtration. The filtrate, combined with ethyl acetate (40 ml) was shaked and the aqueous layer was separated. The aqueous layer was cooled with ice and adjusted to pH 2–3 with 2N-HCl. Precipitated crystals were filtered, washed with water, and dried in vacuo over phosphorus pentoxide to give the title compound (3.53 g). Further, the filtrate was extracted three times with 40 ml each of ethyl acetate. The ethyl acetate layer was dried over anhydrous magnesium sulfate, and concentrated under reduced pressure to give the title compound (0.3 g). The $^1$H-NMR spectrum of this product agreed with that of the product of Example 1.

EXAMPLE 3

Pivaloyloxymethyl 7-[(Z)-2-methoxyimino-2-(thiazol-4-yl)acetamido]-3-carbamoyloxymethyl-3-cephem-4-carboxylate To a solution of sodium 7-[(Z)-2-methoxyimino-2-(thiazol-4-yl)acetamido]-3-carbamoyloxymethyl-3-cephem-4-carboxylate (0.86 g) in dimethylsulfoxide (8 ml) was added pivaloyloxymethyl iodide (0.67 g). This reaction mixture was stirred for 100 min. at room temperature, and then added to a mixture of water (86 ml) and ethyl acetate (86 ml) with stirring. The ethyl acetate layer was separated, washed twice with water, and dried over anhydrous magnesium sulfate. The ethyl acetate was evaporated under reduced pressure. Petroleum ether was added to the residue. Filtration of resulting crystals and drying thereof under reduced pressure gave the title compound (0.67 g) in crude form. This crude product was purified by chromatography on a reverse phase column (LiChroprep® RP-8) with a mobile phase consisting of water-acetonitrile-acetic acid (650:350:5), and the fractions containing the product were freeze-dried. The product thus obtained was contaminated with 2-cephem isomer.

EXAMPLE 4

Pivaloyloxymethyl
7-[(Z)-2-methoxyimino-2-(thiazol-4-yl)acetamido]-3-carbamoyloxymethyl-3-cephem-4-carboxylate-1-oxide The product (0.2 g) obtained in Example 3, i.e. a mixture of pivaloyloxymethyl 7-[(Z)-2-methoxyimino-2-(thiazol-4-yl)acetamido]-3-carbamoyloxymethyl-3-cephem-4-carboxylate and 2-cephem isomer thereof, was dissolved in chloroform (1 ml). To this solution was added dropwise a solution of m-chloroperbenzoic acid (0.059 g) in chloroform (1 ml). The mixture was stirred for 1.5 hours at room temperature. Precipitated crystals were filtered, washed with chloroform (2 ml), and dried under reduced pressure to give the title compound (0.092 g).

$^1$H-NMR (DMSO-$d_6$) δ value: 1.17 (s, 9H), 3.77 (ABq, overlapping with weat peaks), 3.94 (s, 3H), 4.51, 5.02 (ABq, 2H, J=13.6 Hz), 5.04 (d, 1H, J=5 Hz), 5.7–6.0 (m, 3H), 6.61 (broad s, 2H), 7.96 (d, 1H, J=2 Hz), 9.09 (d, 1H, J=8 Hz), 9.13 (d, 1H, J=2 Hz).

EXAMPLE 5

Pivaloyloxymethyl
7-[(Z)-2-methoxyimino-2-(thiazol-4-yl)acetamido]-3-carbamoyloxymethyl-3-cephem-4-carboxylate The 1-oxide derivative (85 mg) from Example 4 was dissolved in dimethylformamide (2 ml, followed by addition of $SnCl_2 \cdot 2H_2O$ (84 mg) and cooling with ice. Acetyl chloride (0.38 ml) was added dropwise to the mixture. Then the ice bath was removed to raise the temperature to 20° C. After stirring for 15 minutes, the reaction mixture was added to cold water (10 ml). The mixture was extracted three times with ethyl acetate (15 ml×3). The ethyl acetate layers, combined together, were washed with water, dried over anhydrous magnesium sulfate, and evaporated to dryness under reduced pressure. The residue was dissolved in ethyl acetate (0.5 ml) and the solution was added dropwise to petroleum ether (30 ml) with stirring. Resulting crystals were filtered, and dried under reduce pressure to give the title compound (35 mg).

$^1$H-NMR (DMSO-$d_6$) δ value: 1.17 (s, 9H), 3.55 (broad s, 2H), 3.91 (s, 3H), 4.57, 4.84 (ABq, 2H, J=13 Hz), 5.21 (d, 1H, J=5 Hz), 5.7–6.0 (m, 3H), 6.60 (broad s, 2H), 7.93 (d, 1H, J=2 Hz), 9.14 (d, 1H, J=2 Hz), 9.67 (d, 1H, J=8 Hz).

EXAMPLE 6

Phthalidyl
7-[(Z)-2-methoxyimino-2-(thiazol-4-yl)acetamido]-3-carbamoyloxymethyl-3-cephem-4-carboxylate Sodium 7-[(Z)-2-methoxyimino-2-(thiazol-4-yl)-acetamido]-3-carbamoyloxymethyl-3-cephem-4-carboxylate (100 mg) was dissolved in dimethylformamide (1 ml). 3-Bromophthalide (69 mg) was added to the solution. After stirring for one hour at room temperature, the reaction mixture was added to a mixture of dil. HCl (10 ml) and ethyl acetate (20 ml). The resulting ethyl acetate layer was separated, washed successively with dil. HCl (10 ml) and saturated aqueous NaCl (10 ml×2), dried over anhydrous magnesium sulfate, and concentrated to dryness under reduced pressure. The residue was dissolved in ethyl acetate (2 ml) and the solution was added dropwise to a petroleum ether-diethyl ether mixture (100 ml) with stirring. Resulting crystals well filtered, and dried under reduced pressure to give the title compound (45 mg).

$^1$N-NMR (DMSO-$d_6$) δ value: 3.61 (broad s, 2H), 3.90 (s, 3H), 4.5–5.0 (m, 2H), 5.1–5.2 (m, 1H), 5.7–5.9 (m, 1H), 6.60 (broad s, 2H), 7.5–8.0 (m, 6H), 9.1–9.2 (m, 1H), 9.5–9.8 (m, 1H).

EXAMPLE 7

1-Acetoxyethyl
7-[(Z)-2-methoxyimino-2-(thiazol-4-yl)acetamido]-3-carbamoyloxymethyl-3-cephem-4-carboxylate To a solution of sodium 7-[(Z)-2-methoxyimino-2-(thiazol-4-yl)acetamido]-3-carbamoyloxymethyl-3-cephem-4-carboxylate (100 mg) in dimethylformamide (1 ml) was added 2-bromoethyl acetate (54 mg). After stirring for 2 hours at room temperature, the reaction mixture was added to a mixture of dil. HCl (10 ml) and ethyl acetate (20 ml). The resulting ethyl acetate layer was separated, washed successively with dil. HCl (10 ml), phosphate buffer (pH 7, 10 ml×2), and saturated aqueous NaCl (10 ml), dried over anhydrous magnesium sulfate, and concentrated to dryness under reduced pressure. The residue was dissolved in ethyl acetate (2 ml), and the solution was added dropwise to a petroleum ether-diethyl ether mixture (100 ml) with stirring. Resulting crystals were filtered, and dried under reduced pressure to give the title compound (50 mg).

$^1$H-NMR (DMSO-$d_6$) δ value: 1.47 (d, 3H, J=5 Hz), 2.05 (s, 3H), 3.57 (broad s, 2H), 3.92 (s, 3H), 4.5–5.3 (m, 3H), 5.8–6.0 (m, 1H), 6.53 (broad s, 2H), 6.8–7.0 (m, 1H), 7.91 (d, 1H, J=2 Hz), 9.13 (d, 1H, J=2 Hz), 9.63 (d, 1H, J=8 Hz).

EXAMPLE 8

1-Ethoxycarbonyloxyethyl
7-[(Z)-2-methoxyimino-2-)thiazol-4-yl)acetamido]-3-carbamoyloxymethyl-3-cephem-4-carboxylate To a solution of sodium 7-[(Z)-2-methoxyimino-2-(thiazole-4-yl)acetamido]-3-carbamoyloxymethyl-3-cephem-4-carboxylate (100 mg) in dimethylformamide (1 ml) was added 1-bromoethoxycarbonyloxyethane (64 mg). The mixture was stirred for 2 hours at room temperature. Then, the reaction mixture was worked up in a manner similar to that described in Example 7, producing the title compound (58 mg).

$^1$H-NMR (DMSO-$d_6$) δ value: 1.23 (t, 3H, J=7 Hz), 1.50 (d, 3H, J=5 Hz), 3.56 (ABq, 2H), 3.91 (s, 3H), 4.17 (q, 2H, J=7 Hz), 5.1–5.3 (m, 1H), 5.8–6.0 (m, 1H), 6.57 (broad s, 2H), 6.7–6.9 (m, 1H), 7.92 (d, 1H, J=2 Hz), 9.14 (d, 1H, J=2 Hz), 9.62 (d, 1H, J=8 Hz).

EXAMPLE 9

(5-Methyl-2-oxo-1,3-dioxolen-4-yl)methyl
7-[(Z)-2-methoxyimino-2-(thiazol-4-yl)acetamido]-3-carbamoyloxymethyl-3-cephem-4-carboxylate To a solution of sodium 7-[(Z)-2-methoxyimino-2-thiazol)-4-yl)acetamido]-3-carbamoyloxymethyl-3-cephem-4-carboxylate (100 mg) in dimethylformamide (1 ml) was added 4-bromethyl-5-methyl-1,3-dioxolen- 2-one (63 mg). The mixture was stirred for 2 hours at room temperature. Then, the reaction mixture was worked up in a manner similar to that described in Example 7, producing the title compound (75 mg).

$^1$H-NMR (DMSO-$d_6$) δ value: 2.17 (s, 3H), 3.57 (broad s, 2H), 3.91 (s, 3H), 4.58, 4.83 (ABq, 2H, J=13 Hz), 5.0–5.3 (m, 3H), 5.6–6.0 (m, 1H), 6.56 (broad s, 2H), 7.93 (d, 1H, J=2 Hz), 9.14 (d, 1H, J=2 Hz), 9.62 (d, 1H, J=8 Hz).

EXAMPLES 10–15

In a manner similar to that described in Example 2, the following compounds were prepared.

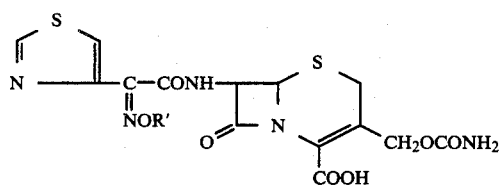

| Example No. | R' | $^1$H—NMR (DMSO-$d_6$) δ value |
|---|---|---|
| 10 | —C$_2$H$_5$ | 1.27 (t, 3H), 3.42, 3.55 (ABq, 2H, J=18 Hz), 4.15 (q, 2H) 4.60, 4.86 (ABq, 2H, J=13 Hz), 5.16 (d, 1H, J=5 Hz), 5.83 (dd, 1H, J=5, 8 Hz), 6.6 (broad s, 2H), 7.94 (d, 1H, J=2 Hz), 9.14 (d, 1H, J=2 Hz), 9.62 (d, 1H, J=8 Hz) |
| 11 | —CH$_2$CH$_2$CH$_3$ | 0.92 (t, 3H), 1.68 (m, 2H), 3.45, 3.58 (ABq, 2H, J=18 Hz), 4.08 (t, 2H), 4.61, 4.87 (ABq, 1H, J=13 Hz), 5.17 (d, 1H, J=5 Hz), 5.83 (dd, 1H, J=5, 8 Hz), 6.4–6.7 (broad s, 2H), 7.92 (d, 2H, J=2 Hz), 9.16 (d, 1H, J=2 Hz), 9.63 (d, 1H, J=8 Hz) |
| 12 | —CH(CH$_3$)$_2$ | 1.25, 1.28 (d × 2, 6H, J=6 Hz), 3.4–3.6 (ABq, overlapping with H$_2$O peaks), 4.40 (m, 1H), 4.63, 4.85 (ABq, 2H, J=13 Hz), 5.17 (d, 1H, J=5Hz), 5.82 (dd, 1H, J=5, 8 Hz), 6.4–6.8 (broad s, 2H), 7.93 (d, 1H, J=2 Hz), 9.16 (d, 1H, J=2 Hz), 9.58 (d, 1H, J=8 Hz) |
| 13 | —(CH$_2$)$_3$CH$_3$ | 0.90 (t, 3H), 1.38 (m, 2H), 1.65 (m, 2H), 3.4–3.6 (ABq, overlapping with H$_2$O peaks), 4.13 (t, 2H), 4.62, 4.87 (ABq, 2H, J=13 Hz), 5.17 (d, 1H, J=5 Hz), 5.82 (dd, 1H, J=5, 8 Hz), 6.3–6.8 (broad s, 2H), 7.92 (d, 1H, J=2 Hz), 9.16 (d, 1H, J=2 Hz), 9.62 (d, 1H, J=8 Hz) |
| 14 | —CH$_2$—CH(CH$_3$)$_2$ | 0.91 (d, 6H, J=7 Hz), 2.02 (m, 1H), 3.4–3.6 (ABq, overlapping with H$_2$O peaks), 3.91 (d, 2H, J=5 Hz), 4.62, 4.88–4.90 (ABq, 2H, J=13 Hz), 5.18 (d, 1H, J=5 Hz), 5.84 (dd, 1H, J=5, 8 Hz), 6.4–6.8 (broad s, 2H), 7.91 (d, 1H, J=2 Hz), 9.14 (d, 1H, J=2 Hz), 9.63 (d, 1H, J=8 Hz) |

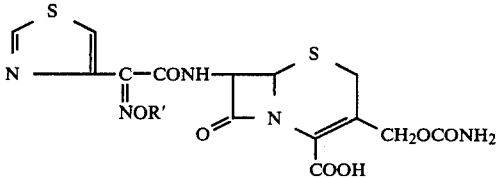

| Example No. | R' | $^1$H—NMR (DMSO-$d_6$) δ value |
|---|---|---|
| 15 | —CH(CH$_3$)CH$_2$CH$_3$ | 0.90 (m, 3H), 1.24 (t, 3H), 1.4–1.8 (m, 2H), 3.45, 3.59 (ABq, 2H, J=18 Hz), 4.19 (m, 1H), 4.62, 4.87 (ABq, 2H, J=13 Hz), 5.19 (d, 1H, J=5 Hz), 5.85 (dd, 1H, J=5, 8 Hz), 6.4–6.8 (broad s, 2H), 7.91 (d, 1H, J=2 Hz), 9.16 (d, 1H, J=2 Hz), 9.58 (d, 1H, J=8 Hz) |

EXAMPLE 16

7-[(Z)-2-hydroxyimino-2-(thiazol-4-yl)acetamido]-3-carbamoyloxymethyl-3-cephem-4-carboxylic acid (a) Z-2-Trityloxyimino-2-(thiazol-4-yl)acetic acid (1.70 g) was dissolved in dimethylformamide (15 ml). Thereto were added 1-hydroxybenzotriazole (0.582 g) and dicyclohexylcarbodiimide (0.861 g). The mixture was stirred for 200 minutes at room temperature, and then filtered to remove the precipitates. The filtrate was added to a solution consisting of 7-amino-3-carbamoyloxymethyl-3-cephem-4-carboxylic acid (1.12 g), triethylamine (0.828 g), and dimethylformamide (10 ml) with stirring. After stirring for 1.5 hours at room temperature, the reaction mixture was added dropwise to diethyl ether (150 ml) with stirring. After removing the ether layer by decantation, the remaining oil was washed further with ether, and dried under reduced pressure to give crude 7-[(Z)-2-trityloxyimino-2-(thiazol-4-yl)acetamido]-3-carbamoyloxymethyl-3-cephem-4-carboxylic acid (1.63 g). The crude product was purified by liquid chromatography [column: Li-Chroprep® RP-8; a mobile phase: pH 6.8 phosphate buffer-acetonitrile (65: 35 vol. ratio)]. The fractions containing the product were combined together, adjusted to pH 2 with 3N-HCl, and extracted with ethyl acetate. Ther extract, i.e. the ethyl acetate solution was dried over anhydrous magnesium sulfate, and concentrated to dryness under reduced pressure to give the intended purified product.

$^1$H-NMR (DMSO-$d_6$) δ value: 3.47, 3.61 (ABq, 2H, J=18 Hz), 4.63, 4.91 (ABq, 2H, J=13 Hz), 5.26 (d, 1H, J=5 Hz), 6.0 (dd, 1H, J=5,8 Hz), 6.6 (broad s, 2H), 7.25–7.5 (m, 15 H), 7.69 (d, 1H, J=2 Hz), 9.11 (d, 1H, J=2 Hz), 9.95 (d, 1H, J=8 Hz).

(b) To a stirring mixture of trifluoroacetic acid (3 ml) and ethyl mercaptan (1 ml) was added 7-[(Z)-2-trityloxyimino-2-(thiazol-4-yl)acetamido]-3-carbamoyloxymethyl-3-cephem-4-carboxylic acid (110 mg). The stirring was continued for 110 min at room temperature. The reaction mixture was concentrated to dryness under reduced pressure at room temperature. Resulting crystals were washed with diethyl ether, and dried in vacuo over calcium chloride to give the title compound (55 mg).

$^1$H-NMR (DMSO-$d_6$) δ value: 3.3–3.7 (C$_2$—H$_2$, overlapping with H$_2$O peaks and other peaks), 4.62, 4.87

What is claimed is:

1. A cephem compound represented by the formula,

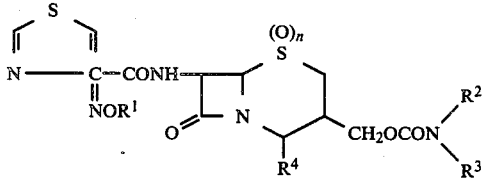

wherein, $R^1$ is methyl or ethyl, $R^2$ and $R^3$ are hydrogen, $R^4$ represents carboxyl or esterified carboxyl, and n represents 0 or 1, or a pharmaceutically acceptable salt of said cephem compound.

2. The compound of claim 1, which is the syn isomer.

3. The compound of claim 1, wherein the residue represented by $R^4$ is carboxyl.

4. The compound of claim 1, wherein $R^4$ is pivaloyloxymethyloxycarbonyl.

5. The compound of claim 1, wherein $R^4$ is 1-ethoxycarbonyloxyethyloxycarbonyl.

6. The compound of claim 1, wherein $R^4$ is 1-acetoxymethyloxycarbonyl.

7. The compound of claim 1, wherein $R^4$ is phthalidyloxycarbonyl.

8. The compound of claim 1, wherein $R^4$ is (5-methyl-2-oxo-1,3-dioxolen-4-yl)methoxycarbonyl.

9. 7-[(Z)-2-methoxyimino-2-(thiazol-4-yl)acetamido]-3-carbamoyloxymethyl-3-cephem-4-carboxylic acid.

10. Pivaloyloxymethyl 7-[(Z)-2-methoxyimino-2-(thiazol-4-yl)acetamido]-3-carbamoyloxymethyl-3-cephem-4-carboxylate.

11. Pivaloyloxymethyl 7-[(Z)-2-methoxyimino-2-(thiazol-4-yl)acetamido]-3-carbamoyloxymethyl-3-cephem-4-carboxylate-1-oxide.

12. 1-Ethoxycarbonyloxyethyl 7-[(Z)-2-methoxyimino-2-(thiazol-4-yl)acetamido]-3-carbamoyloxymethyl-3-cephem-4-carboxylate.

13. 1-Acetoxyethyl 7-[(Z)-2-methoxyimino-2-(thiazol-4-yl)acetamido]-3-carbamoyloxymethyl-3-cephem-4-carboxylate.

14. Phthalidyl 7-[(Z)-2-methoxyimino-2-(thiazol-4-yl)-acetamido]-3-carbamoyloxymethyl-3-cephem-4-carboxylate.

15. An antibiotic composition which comprises a compound as claimed in claim 1 and a pharmaceutically acceptable carrier or diluent.

16. The compound of claim 2, wherein the residue represented by $R^4$ is carboxyl.

17. The compound of claim 1, wherein the esterified carboxyl is represented by —COOR, where R represents lower alkanoyloxyalkyl, lower alkoxycarbonyloxyalkyl, lower alkyl, lower alkenyl, lower alkynyl, lower alkoxyalkyl, lower alkylthioalkyl, lower alkanesulfonylalkyl, benzyl, 4-methoxybenzyl, phenethyl, 3-chlorobenzyl, 3-fluorobenzyl, 3-methylbenzyl, 3-methoxybenzyl, 4-methoxybenzyl, 3,4-dimethoxybenzyl, 2-furylmethyl, 2-thienylmethyl, phenyl, tolyl, xylyl, indanyl, phenacyl, p-chlorophenacyl, 5-lower alkyl substituted-2-oxo-1,3-dioxolen-4-ylmethyl, or phthalidyl.

18. The compound of claim 2, wherein the esterified carboxyl is represented by —COOR where R represents lower alkanoyloxyalkyl, lower alkoxycarbonyloxyalkyl, lower alkyl, lower alkenyl, lower alkynyl, lower alkoxyalkyl, lower alkylthioalkyl, lower alkanesulfonylalkyl, benzyl, 4-methoxybenzyl, phenethyl, 3-chlorobenzyl, 3-fluorobenzyl, 3-methylbenzyl, 3-methoxybenzyl, 4-methoxybenzyl, 3,4-dimethoxybenzyl, 2-furylmethyl, 2-thienylmethyl, phenyl, tolyl, xylyl, indanyl, phenacyl, p-chlorophenacyl, 5-lower alkyl substituted-2-oxo-1,3-dioxolen-4-ylmethyl, or phthalidyl.

19. (5-Methyl-2-oxo-1,3-dioxolen-4-ylmethyl 7-[(Z)-2-methoxyimino-2-(thiazol-4-yl)acetamido]-3-carbamoyloxymethyl-3-cephem-4-carboxylate.

20. A method of treating microbial infections in patients which comprises:
administering to patients an antimicrobially effective amount of the compound of claim 1 or a pharmaceutically acceptable salt thereof.

* * * * *